United States Patent [19]

Hattori et al.

[11] Patent Number: 5,741,687

[45] Date of Patent: Apr. 21, 1998

[54] SORBITOL OXIDASE REAGENT FROM XANTHOMONAS

[75] Inventors: Shizuo Hattori, Tsuruga; Yukihiro Sogabe; Shigenori Emi, both of Turuga, all of Japan

[73] Assignee: Toyo Boseki Kaubshiki Kaisha, Osaka, Japan

[21] Appl. No.: 471,388

[22] Filed: Jun. 6, 1995

Related U.S. Application Data

[62] Division of Ser. No. 162,628, Dec. 7, 1993, Pat. No. 5,472,862.

[30] Foreign Application Priority Data

Dec. 7, 1992 [JP] Japan ................................. 4-326871

[51] Int. Cl.⁶ ....................................................... C12N 9/04
[52] U.S. Cl. ...................... 435/189; 435/190; 435/252.1; 435/25
[58] Field of Search .................................... 435/189, 190, 435/910, 252.1, 25, 975

[56] References Cited

U.S. PATENT DOCUMENTS

| | | | |
|---|---|---|---|
| 5,081,016 | 1/1992 | Hayashi et al. | 435/25 |
| 5,124,254 | 6/1992 | Hewlins et al. | 435/25 |

OTHER PUBLICATIONS

Yamaki et al., *J. Japan Soc. Hort. Sci.* 57(4): 602–607 (1989).
Yamaki, *Plant & Cell Physiol.* 23(5): 891–899 (1982).
Moriguchi et al., *J. Amer. Soc. Hort. Sci.* 115(2): 278–281 (1990).
Yamaki et al., *J. Amer. Hort. Sci.* 111(1): 134–137 (1986).
Yamaki, *Plant & Cell Physiol.* 21(4): 591–599 (1980).
Yamaki, *Plant & Cell Physiol.* 28(4): 557–564 (1987).

*Primary Examiner*—Leon B. Lankford, Jr.
*Attorney, Agent, or Firm*—Foley & Lardner

[57] ABSTRACT

The sorbitol oxidase of the present invention catalyzes the reaction in which D-sorbitol is oxidized D-glucose and hydrogen peroxide.

6 Claims, 5 Drawing Sheets

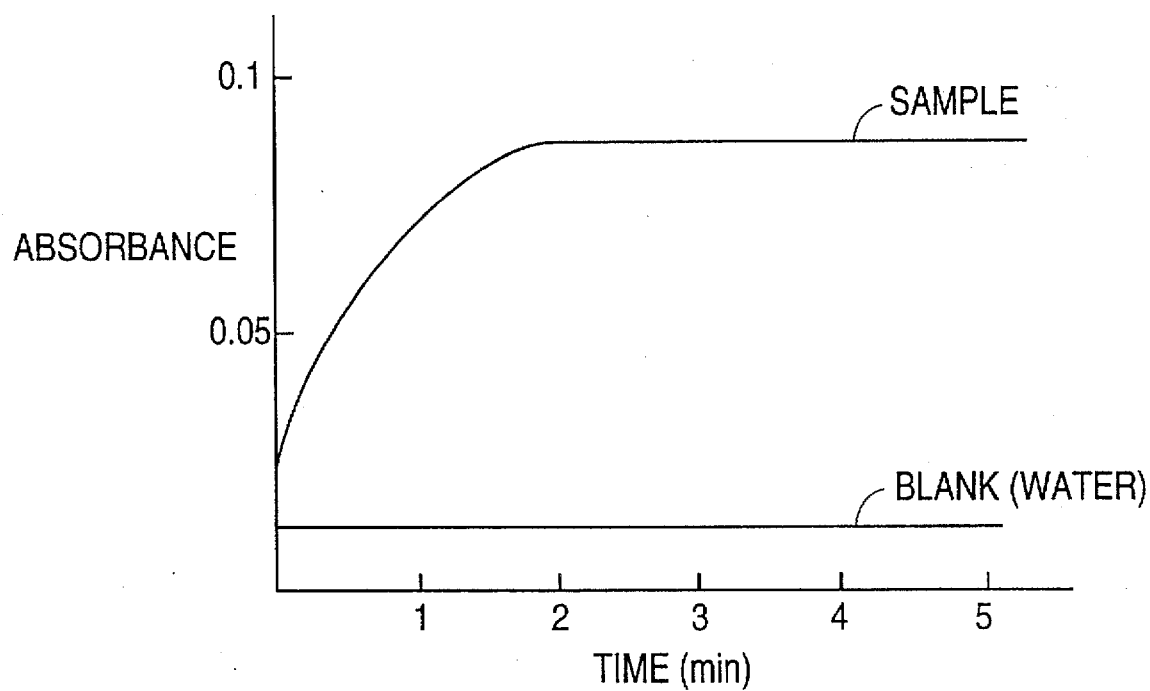

SORBITOL OXIDASE REAGENT FROM XANTHOMONAS

This application is a divisional of application Ser. No. 08/162,628, filed Dec. 7, 1993 now U.S. Pat. No. 5,472,862.

BACKGROUND OF THE INVENTION

1. Field of the Invention

The present invention relates to a novel enzyme, sorbitol oxidase, a process for producing the same, and the use thereof.

2. Description of the Related Art

Up to now, sorbitol oxidase, a novel enzyme, which catalyzes a reaction in which D-sorbitol is oxidized to D-glucose and hydrogen peroxide has not been found. Sorbitol is a compound which is produced in vivo from glucose by aldose reductase. Because sorbitol has poor membrane permeability, the sorbitol has a tendency to be accumulated in a cell such as a red blood cell. The accumulation of sorbitol causes functional disorders such as the increase in an osmotic pressure in vivo, the swelling of a cell, etc. Each of the functional disorders is considered as one of the diabetic complications. Thus, the content of sorbitol in a red blood cell derived from a body can be used for the diagnosis of diabetic complications.

Recently, a number of blocking agents for aldose reductase have been developed as therapeutic agents for diabetic complications. For confirming the effects of these therapeutic agents, the measurement of sorbitol in a red blood cell has been the subject of serious studies paid much attention to.

A sorbitol dehydrogenase (L-Iditol: $NAD^+$ 2-oxidoreductase (EC. 1.1.1.14)), which catalyzes the following reaction, has been used as a method for determining D-sorbitol.

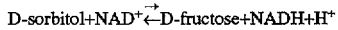

According to the above method, a sorbitol dehydrogenase is allowed to react with D-sorbitol in a biological sample to produce NADH. Then, the NADH thus produced is measured, thereby determining the content of D-sorbitol in the biological sample. However, this method has the following problems.

Since the molecular extinction coefficient of NADH is small, the sensitivity of the measurement is low. In addition, for measuring the NADH with good sensitivity, a special apparatus is required. That is, the NADH is measured with good sensitivity by fluorometry at a wavelength of 366 nm (excitation) and 452 nm (emission). Moreover, NADH, $NAD^+$, etc., which are included in the biological sample may hinder the sensitivity of the measurement.

Another method for determining D-sorbitol, using the above-mentioned sorbitol dehydrogenase has been utilized, in which an artificial electron receptor is used. This method is more useful than the above-mentioned method for measuring NADH; however, the sensitivity for the measurement in this method is not sufficiently precise for clinical diagnosis. Further, sorbitol dehydrogenase is a membrane-bound enzyme, so that it is unstable and tends to be inactivated.

In order to overcome the above-mentioned problems involved in the determination of D-sorbitol, attempts to develop another enzyme such as a sorbitol oxidase have been tried, but have not been found.

SUMMARY OF THE INVENTION

The inventors of the present invention earnestly studied the problems involved in the determination of D-sorbitol using a conventional sorbitol dehydrogenase; as a result, the inventors found a microorganism producing a sorbitol oxidase from the soil of Sekigahara-cho, Fuwa-gun, Gifu Prefecture, Japan, thereby achieving the present invention.

The sorbitol oxidase of this invention catalyzes a reaction in which D-sorbitol is oxidized to D-glucose and hydrogen peroxide.

In one embodiment of the present invention, the above-mentioned sorbitol oxidase has the following physico-chemical characteristics:

(1) Enzyme action: catalyzes the following reaction:

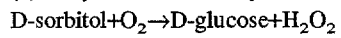

(2) Substrate specificity:
specific activity for D-sorbitol, D-mannitol, D-xylitol, and D-arabitol.

(3) Optimum pH: 6.5 to 7.5, and (4) Molecular weight: about 54,000 (gel filtration) about 43,000 (SDS-PAGE)

According to another aspect of the present invention, a process for producing a sorbitol oxidase comprises the steps of:

cultivating a sorbitol oxidase-producing microorganism which belongs to the genus Xanthomonas in a nutrient culture;

producing the sorbitol oxidase; and collecting the sorbitol oxidase.

In one embodiment of the present invention, the sorbitol oxidase-producing microorganism is *Xanthomonas maltophilia* TE3539.

According to another aspect of the present invention, a method for determining a polyol in a sample, comprises the steps of:

allowing the above-mentioned sorbitol oxidase to react with a sample containing at least one polyol selected from the group consisting of D-sorbitol, D-mannitol, D-xylitol, and D-arabitol;

measuring a generated hydrogen peroxide produced by a reaction or D-glucose, D-mannose, D-xylose, or D-arabinose produced by the reaction, or oxygen consumed during the reaction;

thereby determining the polyol.

In one embodiment of the present invention, the sample comprises a liquid which is prepared from a food stuff or biological sample such as a red blood cell, especially which is prepared by treating a red blood cell obtained by heparinized blood collection.

According to another aspect of the present invention, the reagent for determining D-sorbitol, includes a sorbitol oxidase which catalyzes the reaction in which D-sorbitol is oxidized to D-glucose and hydrogen peroxide.

In one embodiment of the present invention, the above-mentioned reagent further comprises 4-aminoantipyrin, phenol derivative or anilin derivative, and peroxidase.

According to another aspect of the present invention, a kit for determining D-sorbitol, comprises a sorbitol oxidase which catalyzes a reaction in which D-sorbitol is oxidized to D-glucose and hydrogen peroxide.

In one embodiment of the present invention, the above-mentioned kit further comprises 4-aminoantipyrin, phenol derivative or aniline derivative, and peroxidase.

Thus, the invention described herein makes possible the advantages of (1) providing a novel sorbitol oxidase which catalyzes a reaction in which D-sorbitol is oxidized to D-glucose and hydrogen peroxide; (2) providing the determination of sorbitol in a sample with good sensitivity, using the sorbitol oxidase; (3) providing the highly sensitive determination of sorbitol in a red blood cell, thereby accurately diagnosing the diabetic complications; (4) providing a reagent, and a kit for accurately diagnosing the complications of diabetes; and (5) providing a method for efficiently producing the sorbitol oxidase.

These and other advantages of the present invention will become apparent to those skilled in the art upon reading and understanding the following detailed description with reference to the accompanying figures.

BRIEF DESCRIPTION OF THE DRAWINGS

FIG. 9 is a graph showing the change of absorbance when D-sorbitol is determined by measuring the amount of produced glucose.

DESCRIPTION OF THE PREFERRED EMBODIMENTS

Figure 1:
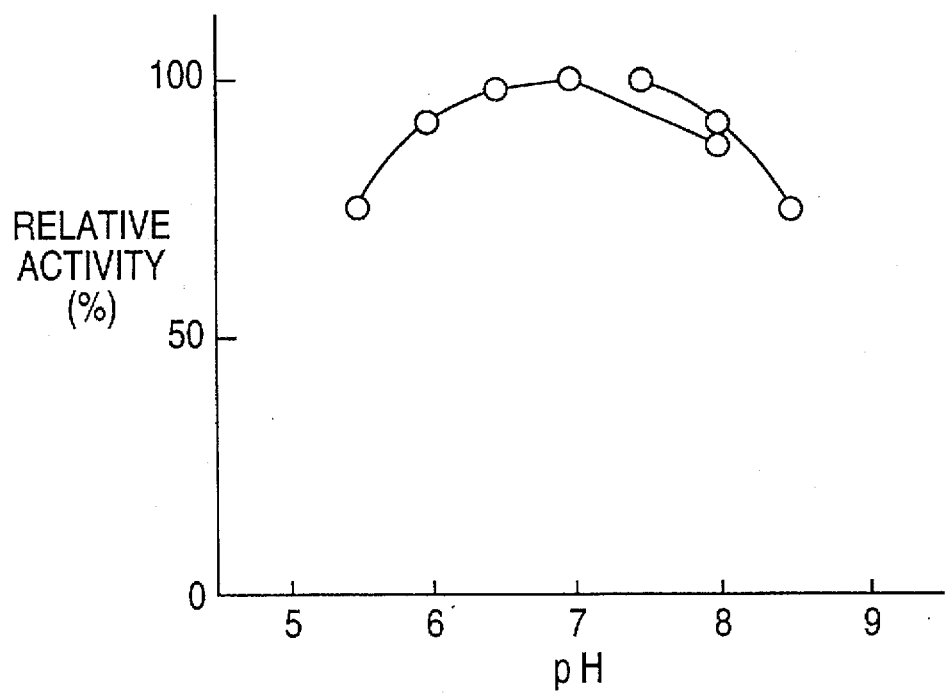
FIG. 1 is a graph showing the relationship between the pH and the relative activity of a sorbitol oxidase of the present invention.

The novel enzyme of the present invention catalyzes the reaction in which D-sorbitol is oxidized to D-glucose and hydrogen peroxide.

The enzyme of the present invention has the following characteristics:

(1) Enzyme action catalyzes the following reaction:

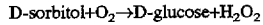

D-sorbitol+$O_2$→D-glucose+$H_2O_2$ (2) Specific activity for D-sorbitol, D-mannitol, D-xylitol, and D-arabitol.

(3) Optimum pH: pH 6.5 to 7.5

(4) Molecular weight: 54,000 (gel filtration) 43,000 (SDS-PAGE)

(5) pH stability: pH 5 to 11

(6) Optimum temperature: 55° C.

(7) Thermostability: up to 50° C.

(8) Isoelectric point: pH 4.0

Any source (e.g., animals, plants, microorganisms, etc.) can be used for the enzyme of the present invention, as long as a sorbitol oxidase having the above-mentioned characteristics can be produced from the source. Preferably, the sorbitol oxidase-producing microorganism belonging to the genus Xanthomonas is used, and the most preferably, *Xanthomonas maltophilia* TE3539 is used. *Xanthomonas maltophilia* TE3539 is a strain isolated from the soil, and its mycological characteristics are as follows:

(a) Morphological characteristics (1) Shape: Short rods (2) Size of a cell: 1.2×0.3 μm (3) Pleomorphism of a cell: None (4) Mobility: Yes, having a polar flagellum (5) Sporulation: None (b) Growth conditions on each medium (1) Broth agar plate medium: After 48 hours of culture at 30° C., a yellow to creme-colored colony is formed. The periphery of the colony is entire and convex. The colony has a smooth, lustered and opaque surface.

(2) Bouillon culture: The strain grows satisfactorily, and the bouillon becomes uniformly turbid.

(3) Gelatin stab culture: The strain grows satisfactorily, and only the upper portion thereof becomes a filiform. The gelatin is liquefied.

(4) Litmus milk: Color is not changed. Milk is solidified.

(c) Physiological characteristics

| | |
|---|---|
| (1) Gram staining: | Negative |
| (2) Reduction of nitrate: | Negative |
| (3) Denitrification: | Negative |
| (4) MR test: | Negative |
| (5) VP test: | Negative |
| (6) Production of indole: | Negative |
| (7) Production of hydrogen sulfide: | Negative |
| (8) Hydrolysis of starch: | Negative |
| (9) Use of citric acid: | |
| Koser's 19 medium: | Negative |
| Christensen's medium: | Positive |
| (10) Production of pigment: Water-soluble yellow pigment is produced in a cell. | |
| (11) Urease: | Negative |
| (12) Oxidase: | Negative |
| (13) Catalase: | Positive |
| (14) β-galactosidase: | Positive |
| (15) Arginine dihydrolase: | Negative |
| (16) Lysine carboxylase: | Negative |
| (17) Ornithine carboxylase: | Negative |
| (18) Tryptophan deaminase: | Negative |
| (19) β-glucosidase: | Negative |
| (20) Protease: | Positive |
| (21) Growth conditions: | |
| Growth temperature | |
| 20° C. | Positive |
| 30° C. | Positive |
| 37° C. | Negative |
| 40° C. | Negative |
| Growth pH | |
| pH 4 | Negative |
| pH 7 | Positive |
| pH 9 | Positive |
| (22) Behavior toward oxygen: Aerobic | |
| (23) O-F test (Hugh Leifson method): (No degradation of sugar) | Negative |
| (24) Production of acid and gas from sugar | |

| | Acid | Gas |
|---|---|---|
| L-arabinose | Negative | Negative |
| D-xylose | Negative | Negative |
| D-glucose | Negative | Negative |
| D-mannose | Positive | Negative |
| D-fructose | Positive | Negative |
| D-galactose | Negative | Negative |
| Maltose | Positive | Negative |
| Sucrose | Negative | Negative |

| -continued | | |
|---|---|---|
| Lactose | Negative | Negative |
| Trehalose | Negative | Negative |
| D-sorbitol | Negative | Negative |
| D-mannitol | Negative | Negative |
| Inositol | Negative | Negative |
| Glycerin | Positive | Negative |
| Starch | Negative | Negative |
| Rhamnose | Negative | Negative |
| D-melibiose | Negative | Negative |
| D-amygdalin | Negative | Negative |
| (25) Utilization of organic compound | | |
| D-glucose | | Positive |
| L-arabinose | | Positive |
| D-mannose | | Positive |
| D-mannitol | | Positive |
| D-sorbitol | | Positive |
| N-acetyl-D-glucosamine | | Negative |
| Maltose | | Positive |
| Potassium gluconate | | Positive |
| n-caprinate | | Negative |
| Adipic acid | | Negative |
| dl-malic acid | | Positive |
| Sodium citrate | | Positive |
| Phenyl acetate | | Negative |

An experiment for identifying the above-mentioned mycological characteristics was conducted in accordance with T. Hasegawa (1985), Revised edition "Classification and identification of microorganisms", Academy publishing center. The classification and identification of microorganisms are based on "Bergey's Manual of Systematic Bacteriology" (1984).

From the literature and mycological characteristics, the above-mentioned strain is decided to belong to the genus Xanthomonas. The strain shares a number of characteristics with *Xanthomonas campestris* or *Xanthomonas maltophilia*. The strain is not recognized to have plant pathogenicity. The strain is recognized to exist singly or in pairs. Moreover, the strain does not produce acid from glucose but produces acid from maltose. Thus, the strain is named as *Xanthomonas maltophilia* TE3539. The strain has been deposited as *Xanthomonas maltophilia* TE3539 in the National Institute of Biosclerics and Human Technology with the accession No. FERM BP-4512.

The enzyme of the present invention can be produced by cultivating the above-mentioned strain, which produces a sorbitol oxidase, in a nutrient medium, and isolating the sorbitol oxidase from the culture thus obtained. Any media such as a synthetic medium and a natural medium can be used for cultivating the strain producing the sorbitol oxidase, as long as the medium contains a carbon source, a nitrogen source, an inorganic substance, and other required nutrients which the microorganism can assimilate. Examples of the carbon source include glucose, glycerol, and the like. Examples of the nitrogen source include natural substances containing nitrogen such as peptones, a broth, a yeast extract, and the like; and compounds containing inorganic nitrogen such as ammonium chloride, ammonium citrate, and the like. Examples of the inorganic substances include potassium phosphate, sodium phosphate, magnesium sulfate, and the like. It is desired that sorbitol is added to the medium as an inducer for producing the sorbitol oxidase.

In general, a microorganism is cultivated by shaking or by an aeration culture. Culture conditions vary depending upon the kind of microorganism. Generally, the culture temperature is in the range of 20° to 35° C., preferably 25° to 30° C.; and the culture pH is in the range of 5 to 9, preferably 6 to 8. The culture period of a microorganism is generally one to seven days. The sorbitol oxidase is produced to be accumulated in the cultured strain.

The enzyme of the present invention can be purified by a conventional method. The enzyme is extracted by a disruption method using ultrasonic waves; a mechanical disruption method using a glass beads, or French press; a method using a surfactant; or the like. Moreover, the extract thus obtained is treated by using an ammonium sulfate, sodium sulfate, etc.; a metal agglutination method using magnesium chloride, calcium chloride, etc.; an agglutination method using protamine, polyethyleneimine, etc.; an ion exchange chromatography methods using resins such as diethylaminoethyl (DEAE)-sephalose, carboxymethyl (CM)-sephalose, etc.; or the like. Accordingly, the enzyme is purified. A crude enzyme solution or purified enzyme solution can be dried or powdered by spray-drying, lyophilization, or the like. Alternatively, the crude enzyme solution or the purified enzyme solution is immobilized on a suitable carrier to be used as immobilized enzyme. A known immobilization method can be employed.

Hereinafter, a method for determining the activity of the sorbitol oxidase of the present invention will be described. The activity of the sorbitol oxidase is determined by measuring $H_2O_2$ produced by the enzyme reaction.

First, the following reaction mixture is prepared.

Substrate solution (0.2M sorbitol in 0.1M potassium-phosphate buffer (pH 7.0)) 50 ml 0.1 w/v % aqueous solution of 4-aminoantipyrin 10 ml 0.1 w/v % aqueous solution of phenol 20 ml 0.025 w/v % aqueous solution of peroxidase (manufactured by Toyo Boseki Kabushiki Kaisha) 20 ml Then, 3.0 ml of the reaction mixture is put in a cuvette and prewarmed at 37° C. for about 5 minutes. To this reaction mixture, 0.05 ml of enzyme solution was added and allowed to react. The absorbance of the reaction mixture at 500 nm is recorded for 3 to 4 minutes by using a spectrophotometer set at 37° C. From the initial linear portion of the absorbance curve thus obtained, the change of absorbance per minute is obtained. As a control, 0.1M potassium-phosphate buffer (pH 7.0) is added instead of the enzyme solution, and the same process is conducted. The one unit (U) of sorbitol oxidase activity is defined as oxidizing 1 μmole of sorbitol per minute under the above conditions.

Further, according to the present invention the amount of polyol can be determined. The sorbitol oxidase having the above-mentioned characteristics is allowed to react with a sample containing at least one polyol selected from the group consisting of D-sorbitol, D-mannitol, D-xylitol, and D-arabitol. Then, hydrogen peroxide thus produced or D-glucose, D-mannose, D-xylose, or D-arabinose thus produced, or oxygen thus consumed is measured, thereby determining the amount of the polyol.

Examples of the sample containing the polyol such as D-sorbitol, D-mannitol, D-xylitol, D-arabitol, etc., include food and biological samples such as a red blood cell.

Hydrogen peroxide produced by the sorbitol oxidase can be measured by using a hydrogen peroxide electrode, a chromogenic method, a fluorescent method, etc. An example of the chromogenic method includes a method using chromogenic agents, such as 4-aminoantipyrin, a phenol derivative, an aniline derivative, benzothiazolinone, etc., to develop color by reacting with peroxidase. An example of the fluorescent method includes a method using an acridinium ester, lumigenine, or derivatives thereof, luminol or a derivative thereof.

D-glucose produced by the sorbitol oxidase can be measured by an ultraviolet absorbance spectrum, using glucose dehydrogenase or hexokinase/glucose-6-dehydrogenase phosphate. Alternatively, the D-glucose is measured by a method using a formazan reaction utilizing diaphorase. D-mannose, D-xylose, and D-arabinose can be measured by a known method.

Oxygen consumed by the sorbitol oxidase can be measured by using a Warburg's manometer, an oxygen electrode, etc.

According to the present invention, the sorbitol oxidase of the present invention is reacted with a sample containing the above-mentioned polyol under the following conditions, and then a product produced by the reaction or oxygen consumed is measured.

A reagent containing the enzyme of the present invention is allowed to react with a sample for 5 to 15 minutes under the conditions of pH 5 to 9, preferably pH 6 to 8, a temperature of not more than 50° C., preferably in the range of 25° to 40° C. As a buffer to be used, a phosphate buffer, a Tris-HCl buffer, borate buffer, and a GOOD's buffer are preferred.

According to the present invention, the polyol can be measured by a Rate method or End method.

According to the present invention, a reagent or a kit containing a sorbitol oxidase is used for measuring sorbitol in a red blood cell. The reagent or kit can contain an agent required for measuring hydrogen peroxide or D-glucose produced by the reaction of the sorbitol oxidase. In the case where hydrogen peroxide is measured, the reagent or kit can contain the above-mentioned chromogenic agent and peroxidase. In the case where D-glucose is measured, the reagent or kit can contain glucose dehydrogenase or hexokinase/glucose-6-dehydrogenase phosphate.

The novel enzyme of the present invention reacts with D-sorbitol to produce D-glucose and hydrogen peroxide. By using this enzyme, polyols such as D-sorbitol, D-mannitol, D-xylitol, D-arabitol, etc. can be efficiently measured. In particular, D-sorbitol is a cause of the diabetic complications, so that a method for measuring D-sorbitol with good sensitivity has been desired for a long time. The use of the sorbitol oxidase of the present invention makes it possible to diagnose the complications of diabetes with good sensitivity.

Hereinafter, the present invention will be described by way of illustrative examples with reference to the drawings.

EXAMPLE 1

First, 100 ml of medium (pH 7.0) containing 1 w/v % sorbitol, 1 w/v % polypsprone, 0.5 w/v % yeast extract, and 0.5 w/v % NaCl in a 500 ml Sakaguchi flask was sterilized in an autoclave at 121° C. for 15 minutes. A loop of *Xanthomonas maltophilia* TE3539 (FERM BP-4512) was inoculated as a seed and cultivated at 30° C. for 48 hr to obtain a seed. Then, 6 l of the above medium in a 10 l jar fermentor was sterilized at 121° C. for 15 minutes, and was cooled. Thereafter, 100 ml of the seed culture was transferred to this medium and cultivated for 2 days under the conditions of 300 rpm, an aeration rate of 2 l/min., and a temperature of 30° C. The culture thus obtained was centrifuged to collect cells. These cells were suspended in 50 mM phosphate buffer (pH 7.0).

The cells thus collected were disrupted by a French press, followed by being centrifuged to obtain a supernatant. The crude enzyme solution thus obtained was purified to a specific activity of 13 U/mg by gel filtration, using the fractionation with ammonium sulfate, DEAE-Sepharose chromatography, phenyl-Sepharose chromatography, and Sephadex G-200.

The sorbitol oxidase thus obtained had the following characteristics:

(1) Catalyzes the following reaction

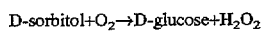

$$D\text{-sorbitol} + O_2 \rightarrow D\text{-glucose} + H_2O_2$$

(2) Substrate specificity

The enzyme activity was determined in the case where various monosaccharides and derivatives thereof were used as a substrate. The value of enzyme activity with respect to D-sorbitol was set at 100.

TABLE 1

| Substrate | Relative activity (%) |
| --- | --- |
| D-sorbitol | 100.00 |
| D-mannitol | 86.60 |
| Inositol | 0.40 |
| D-xylitol | 89.90 |
| D-arabitol | 23.20 |
| Glycerol | 3.50 |
| D-glucose | 0.54 |
| D-fructose | 2.88 |
| D-galactose | 0.42 |
| D-mannose | 1.01 |
| L-sorbose | 10.60 |
| Maltose | 0.00 |
| D-glucosamine hydrochloride | 0.00 |

(3) Km value

The Km value with respect to sorbitol was 0.60 mM.

(4) Optimum pH

The enzyme activity was determined in 50 mM potassium-phosphate buffer (pH 5.5 to 8.0) and 50 mM Tris-HCl buffer (pH 7.5 to 8.5). The results are shown in FIG. 1. The optimum pH was 6.5 to 7.5.

(5) pH stability

Figure 2:
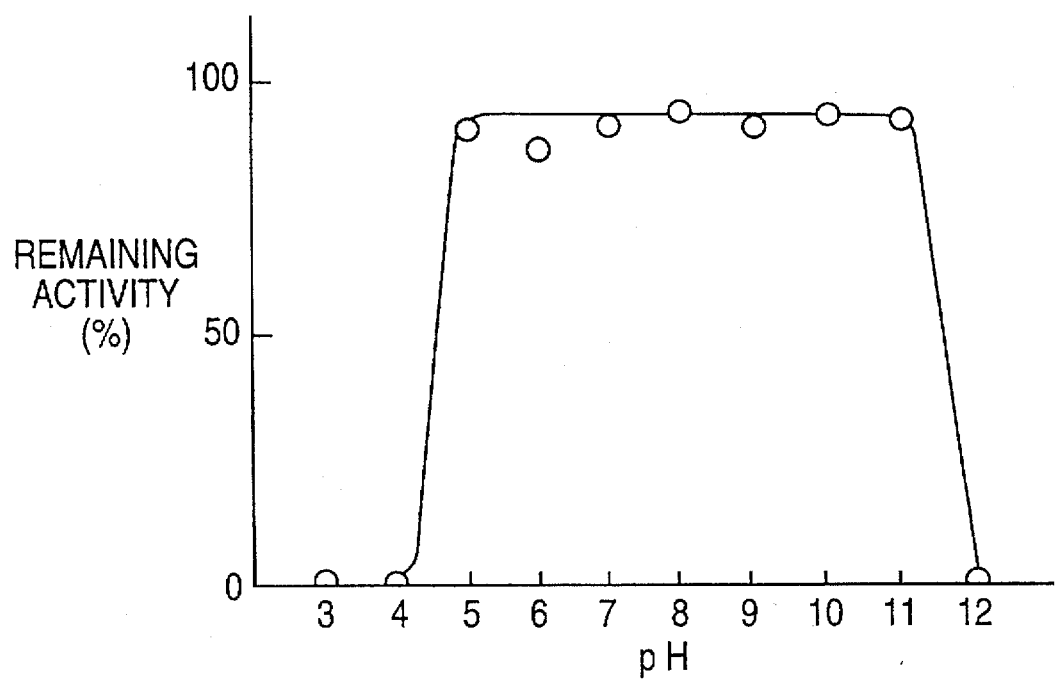
FIG. 2 is a graph showing the pH stability of the sorbitol oxidase of the present invention.

The sorbitol oxidase was kept in a Britton-Robinson's buffer (pH 3 to 12) at 25° C. for 24 hours to determine residual activity thereof. The results are shown in FIG. 2. The stable pH is 5 to 11.

(6) Optimum temperature

Figure 3:
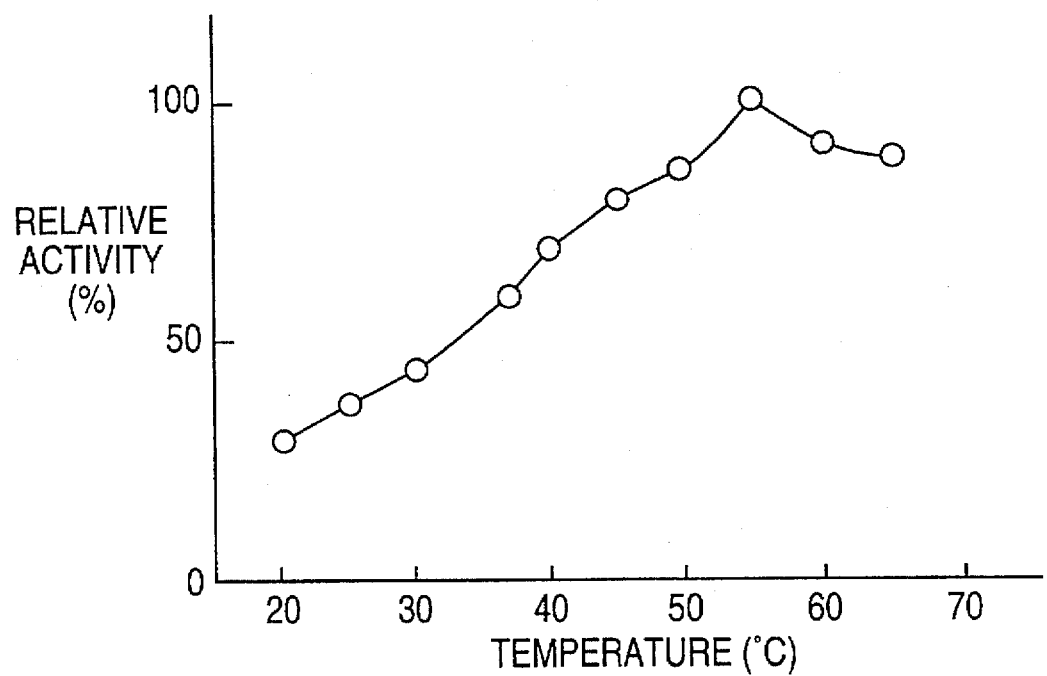
FIG. 3 is a graph showing the relationship between the reaction temperature and the relative activity of the sorbitol oxidase of the present invention.

The enzyme activity at each temperature was determined. The results are shown in FIG. 3. The optimum temperature was 55° C.

(7) Thermostability

Figure 4:
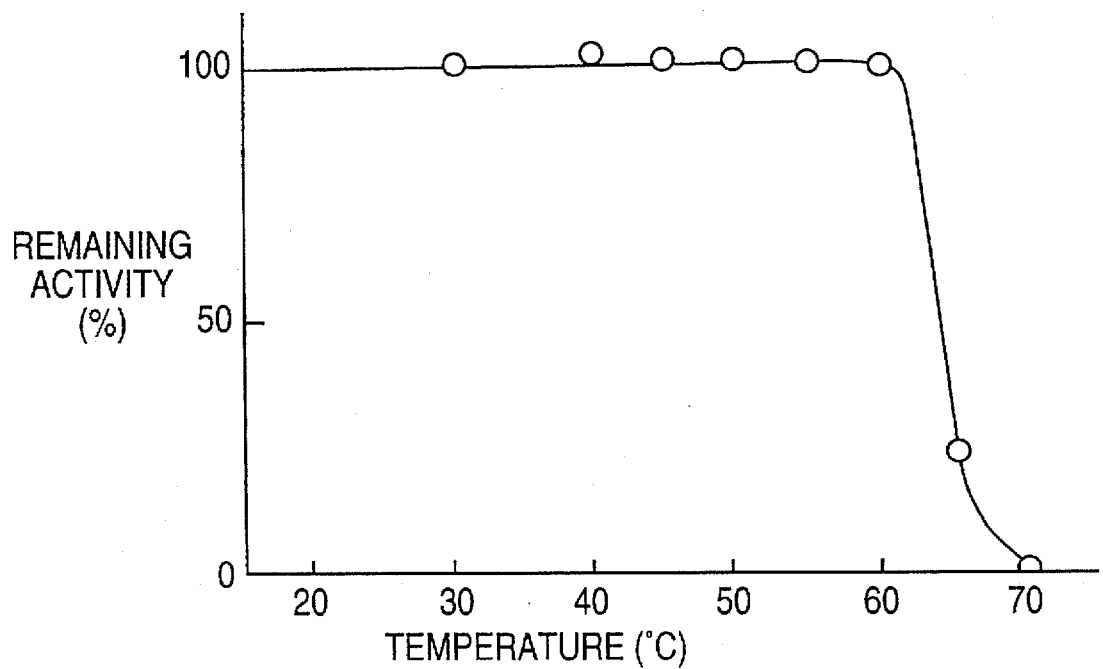
FIG. 4 is a graph showing the thermal stability of the sorbitol oxidase of the present invention.

The enzyme of the present invention was kept in 50 mM potassium-phosphate buffer (pH 8.0) for 15 minutes. Thereafter, the residual enzyme activity was determined. The results are shown in FIG. 4. The residual enzyme activity was stable up to 60° C.

(8) Molecular weight: 54,000 (gel filtration) 43,000 (SDS-PAGE)

(9) Isoelectric point: pH 4.0 (isoelectric focusing)

(10) Absorption spectrum

Figure 5:
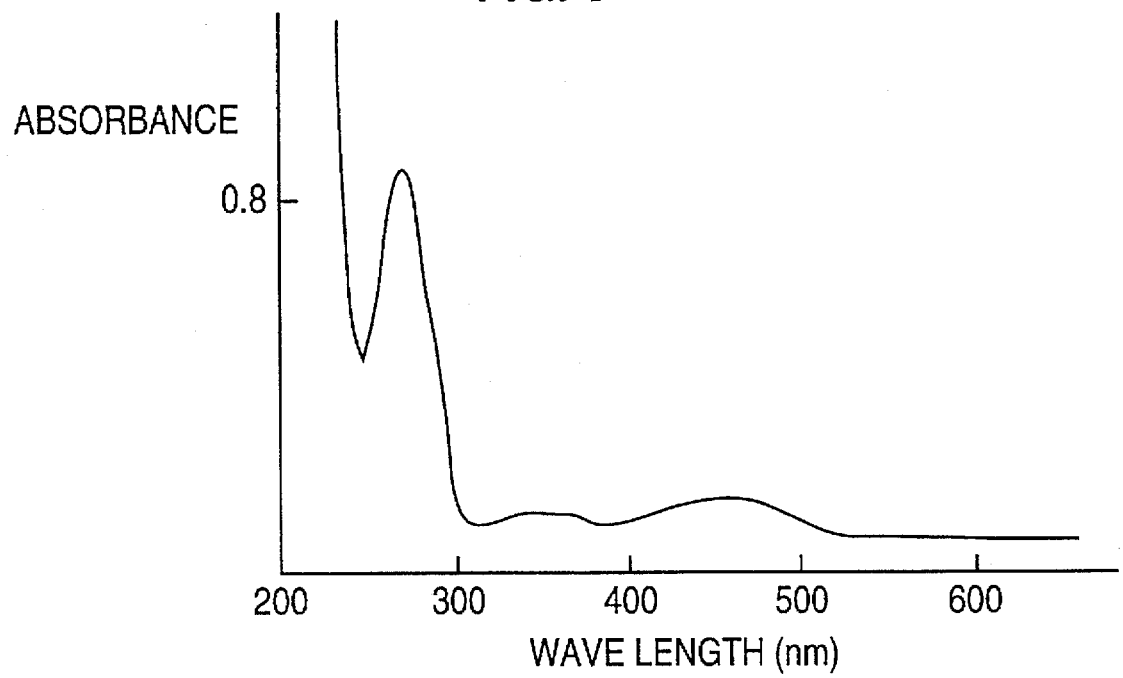
FIG. 5 is a graph showing an absorption spectrum of the sorbitol oxidase of the present invention.

The purified enzyme had a sharp peak at 273 nm and broad peaks at 350 nm and 450 nm, thus showing a typical pattern of flavin enzyme (FIG. 5).

EXAMPLE 2

Figure 6:
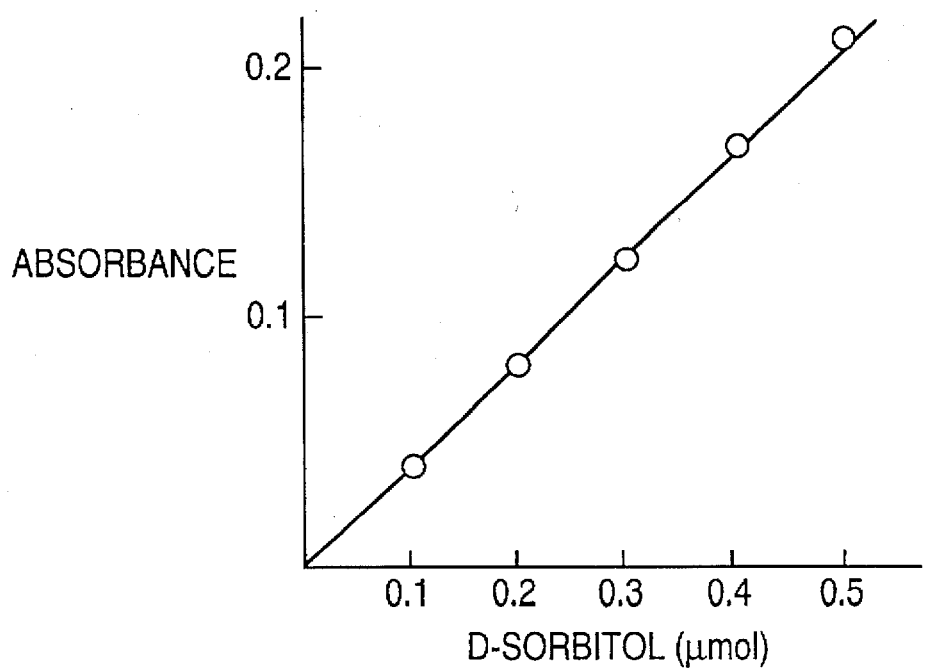
FIG. 6 is a standard curve showing the relationship between the amount of D-sorbitol and the absorbance at 500 nm by the use of the sorbitol oxidase of the present invention.

As a reaction solution, a reaction reagent containing 50 mM phosphate buffer (pH 7.0), 0.50 mM 4-aminoantipyrin, 2.0 mM phenol, 4.5 U/ml of peroxidase (manufactured by Toyo Boseki Kabushiki Kaisha), and 1 U/ml of enzyme of the present invention Was prepared. Then, 0.05 ml each of sample solutions (6 kinds) was respectively added to 1 ml of the reaction reagent this case, 6 kinds of sample solutions contained 0, 0.1, 0.2, 0.3, 0.4, and 0.5 μmole of D-sorbitol, respectively. Each mixture (i.e., 0.05 ml of the sample solution and 1 ml of the reaction reagent) was allowed to react at 37° C. for 5 minutes, and the absorbance of each mixture was measured at 500 nm by a spectrophotometer. The results are shown in FIG. 6. As is understood from this figure, the relationship between the absorbance and the amount of D-sorbitol (i.e., standard curve) was expressed as a straight line in the range of 0 to 0.5 µmole of D-sorbitol. Thus, in this range, it was possible to measure D-sorbitol.

EXAMPLE 3

Figure 7:
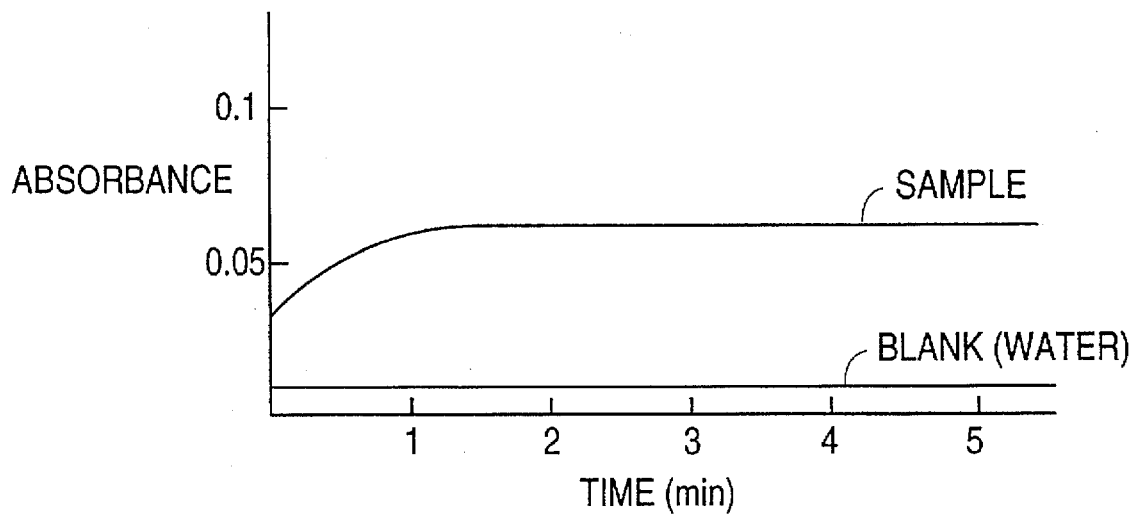
FIG. 7 is a graph showing the change of absorbance when D-sorbitol in a red blood cell is measured.

From blood obtained by heparinized blood collection, a 2 ml packed cell of red blood cells was prepared. Then, 3 ml of cooled (4%) perchloric acid was added to the packed cell to remove proteins. To the supernatant thus obtained, 0.25 ml of 2.5M potassium carbonate was added, mixed and allowed to stand at 4° C. for 2 hours. Then, the mixture was centrifuged to obtain a supernatant as a sample. Then, 0.05 ml of the sample was mixed with 1 ml of the reaction reagent prepared in Example 2. The mixture thus obtained was allowed to react at 37° C., FIG. 7 shows the change of the absorbance of the mixture at 500 nm with time.

Comparative Example 2

Figure 8:
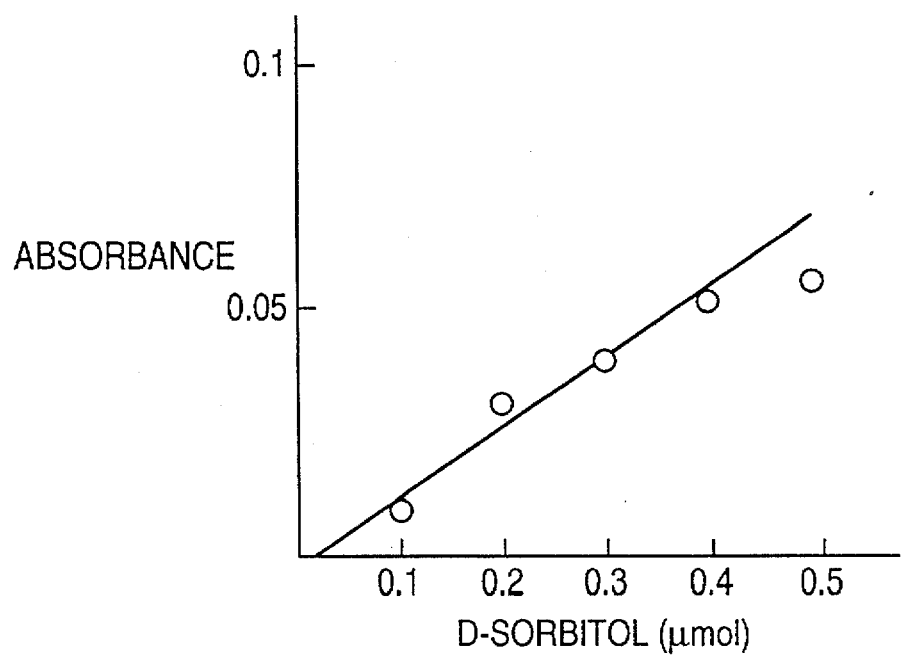
FIG. 8 is a standard curve showing the relationship between the amount of D-sorbitol and the absorbance at 340 nm by the use of a sorbitol dehydrogenase.

As a reaction solution, a reaction reagent containing Tris-HCl buffer (pH 8.0), 4 mM $NAD^+$, and 5 U/ml of sorbitol dehydrogenase (manufactured by Boehringer) was prepared. Then, 0.05 ml each of sample solutions (6 kinds) was respectively added to 1 ml of the reaction reagent. In this case, the 6 kinds of sample solutions contained 0, 0.1, 0.2, 0.3, 0.4, and 0.5 µmole of D-sorbitol. Each mixture (i.e., 0.05 ml of the sample solution and 1 ml of the reaction reagent) was allowed to react at 37° C. for 30 minutes, and the absorbance of each mixture was measured at 340 nm by a spectrophotometer. The results are shown in FIG. 8. This measurement was poor in sensitivity, and a calibration curve did not have linearity sufficient for measurement.

EXAMPLE 4

First, 0.05 ml each of sample solutions (3 kinds) was added to 1 ml of the reaction reagent prepared in Example 2. In this case, the 3 kinds of sample solutions contained 0.1 µmole of D-mannitol, 0.1 µmole of D-xylitol, and 0.1 µmole of D-arabitol, respectively. Each mixture (i.e., 0.05 ml of the sample solution and 1 ml of the reaction reagent) was allowed to react at 37° C. for 5 minutes, and the absorbance of each mixture was measured by a spectrophotometer at 500 nm. The results showed that the respective absorbances were 0.042 (D-mannitol), 0.044 (D-xylitol), and 0.040 (D-arabitol). Thus, these absorbances were almost the same as that of D-sorbitol, i.e., 0.042.

EXAMPLE 5

A reaction reagent containing 50 mM Tris-HCl buffer (pH 8.0), 4 mM $NAD^+$, 30 U/ml of glucose dehydrogenase (manufactured by Toyo Boseki Kabushiki Kaisha), and 1 U/ml of the enzyme of the present invention was prepared. Then, 0.05 ml of sample solution containing 0.5 µmole of D-sorbitol was added to the reaction reagent. The mixture thus obtained was allowed to react, and the absorbance of the mixture was obtained at 340 nm by a spectrophotometer. Due to the reaction of the enzyme of the present invention, D-glucose was produced from D-sorbitol. The present example showed that D-sorbitol could be measured by the amount of D-glucose produced.

Various other modifications will be apparent to and can be readily made by those skilled in the art without departing from the scope and spirit of this invention. Accordingly, it is not intended that the scope of the claims appended hereto be limited to the description as set forth herein, but rather that the claims be broadly construed.

What is claimed is:

1. A reagent for determining sorbitol, which comprises sorbitol oxidase that catalyzes the following reaction: sorbitol+$O_2$→glucose+and hydrogen peroxide, wherein the sorbitol oxidase is isolated from *Xanthomonas maltophilia* and wherein said sorbitol oxidase further has the following properties:

(1) substrate specificity: specific activity for D-sorbitol, D-mannitol, D-xylitol, and D-arabitol;

(2) optimum pH: 6.5 to 7.5; and (3) molecular weight: about 54,000 as determined by gel filtration or about 43,000 as determined by SDS-PAGE.

2. The reagent of claim 1, wherein the sorbitol oxidase is isolated from *Xanthomonas maltophilia* FERM BP-4512.

3. A kit for determining D-sorbitol, which comprises sorbitol oxidase that catalyzes the following reaction: sorbitol+$O_2$→glucose+$H_2O_2$ and is isolated from *Xanthomonas maltophilia*, and wherein said sorbitol oxidase further has the following properties:

(1) substrate specificity: specific activity for D-sorbitol, D-mannitol, D-xylitol, and D-arabitol;

(2) optimum pH: 6.5 to 7.5; and (3) molecular weight: about 54,000 as determined by gel filtration or about 43,000 as determined by SDS-PAGE.

4. A kit of claim 3, wherein said sorbitol oxidase is isolated from *Xanthomonas maltophilia* FERM BP-4512.

5. The reagent of claim 1, which further comprises 4-aminoantipyrin, phenol derivatives or aniline derivative and peroxidase.

6. The kit of claim 3, which further comprises aminoantipyrin, phenol derivatives or aniline derivative and peroxidase.

* * * * *